US009597461B2

(12) United States Patent
Aasmul

(10) Patent No.: US 9,597,461 B2
(45) Date of Patent: *Mar. 21, 2017

(54) INJECTION APPARATUS AND SPECIAL NEEDLE FOR MAKING AN INJECTION AT A PREDETERMINED DEPTH IN THE SKIN

(75) Inventor: Søren Aasmul, Holte (DK)

(73) Assignee: MEDTRONIC MINIMED, INC., Northridge, CA (US)

( * ) Notice: Subject to any disclaimer, the term of this patent is extended or adjusted under 35 U.S.C. 154(b) by 1323 days.

This patent is subject to a terminal disclaimer.

(21) Appl. No.: 12/673,847

(22) PCT Filed: Aug. 14, 2008

(86) PCT No.: PCT/EP2008/060664
§ 371 (c)(1),
(2), (4) Date: Feb. 17, 2010

(87) PCT Pub. No.: WO2009/024522
PCT Pub. Date: Feb. 26, 2009

(65) Prior Publication Data
US 2011/0172636 A1 Jul. 14, 2011

(30) Foreign Application Priority Data
Aug. 17, 2007 (GB) .................................. 0716159.9

(51) Int. Cl.
*A61M 5/42* (2006.01)
*A61M 5/32* (2006.01)
(Continued)

(52) U.S. Cl.
CPC ...... *A61M 5/3286* (2013.01); *A61M 37/0069* (2013.01); *B24B 19/16* (2013.01);
(Continued)

(58) Field of Classification Search
CPC .. A61M 2005/1581; A61M 2005/1585; A61M 37/0069; A61M 5/158;
(Continued)

(56) References Cited

U.S. PATENT DOCUMENTS 2,716,983 A 9/1955 Windischman et al.
3,308,822 A * 3/1967 De Luca ............. A61M 5/3286
604/274

(Continued)

FOREIGN PATENT DOCUMENTS

EP 0 995 453 A1 4/2000
EP 1 297 856 A1 4/2003
(Continued)

OTHER PUBLICATIONS

Extract from www.harvardapparatus.com.
(Continued)

*Primary Examiner* — Quynh-Nhu H Vu
(74) *Attorney, Agent, or Firm* — Nixon & Vanderhye P.C.

(57) ABSTRACT

An injection apparatus for making an injection at a predetermined depth in skin comprises: a skin positioning member, an injection needle (610), and means guiding the injection needle for movement from a parking position above the skin beside said skin positioning member to slide beneath said skin positioning member to an injection position; wherein: the tip (620) of the injection needle is closer to the longitudinal axis of the shaft portion (650) than is the outside of the shaft portion (650) and/or the length of the lumen opening (625) of the needle is in a range from 5 to 15 times the diameter of the shaft (650) of the needle. An injection needle wherein the length of the lumen opening (625) of the needle is in a range from 5 to 15 times the diameter of the shaft (650) of the needle.

14 Claims, 14 Drawing Sheets

(51) Int. Cl.
*A61M 37/00* (2006.01)
*B24B 19/16* (2006.01)
*A61B 5/145* (2006.01)
*A61M 5/158* (2006.01)

(52) U.S. Cl.
CPC ..... *A61B 5/14532* (2013.01); *A61B 2560/063* (2013.01); *A61M 5/158* (2013.01); *A61M 5/3287* (2013.01); *A61M 2005/1581* (2013.01); *A61M 2005/1585* (2013.01)

(58) Field of Classification Search
CPC .............. A61M 5/3286; A61M 5/3287; A61B 2560/063; A61B 5/14532; B24B 19/16
USPC .............. 604/506, 115–117, 164.04, 164.06, 604/164.12, 174, 179–181
See application file for complete search history.

(56) References Cited

U.S. PATENT DOCUMENTS

| | | | | |
|---|---|---|---|---|
| 3,324,854 | A | * | 6/1967 | Weese .................... A61M 5/425 604/115 |
| 4,299,219 | A | * | 11/1981 | Norris, Jr. ............. A61M 5/425 604/115 |
| 5,254,106 | A | * | 10/1993 | Feaster ......................... 604/272 |
| 5,484,403 | A | | 1/1996 | Yoakum et al. |
| 5,968,022 | A | * | 10/1999 | Saito ............................. 604/272 |
| 2002/0173769 | A1 | * | 11/2002 | Gray .................... A61M 5/1456 604/506 |
| 2003/0171716 | A1 | * | 9/2003 | Ejlersen ......................... 604/117 |
| 2004/0158136 | A1 | * | 8/2004 | Gough ............... A61B 5/14546 600/328 |
| 2006/0178646 | A1 | | 8/2006 | Harris et al. |
| 2006/0276759 | A1 | * | 12/2006 | Kinast ................. A61M 5/3286 604/272 |
| 2008/0015624 | A1 | * | 1/2008 | Sonoda ................. A61M 5/158 606/185 |
| 2009/0192486 | A1 | | 7/2009 | Wilmot et al. |
| 2010/0137799 | A1 | * | 6/2010 | Imai ..................... A61M 5/158 604/115 |

FOREIGN PATENT DOCUMENTS

| | | |
|---|---|---|
| JP | 9276403 A | 10/1997 |
| WO | WO 00/02048 | 1/2000 |
| WO | WO 02/30275 A1 | 4/2002 |
| WO | WO 2005/016420 A1 | 2/2005 |

OTHER PUBLICATIONS

Extract from www.connhypo.com.
International Standard, "Sterile Hypodermic Needles for Single Use", ISO 7864, May 1993.
International Search Report for PCT/EP2008/060664, mailed Nov. 24, 2008.

\* cited by examiner

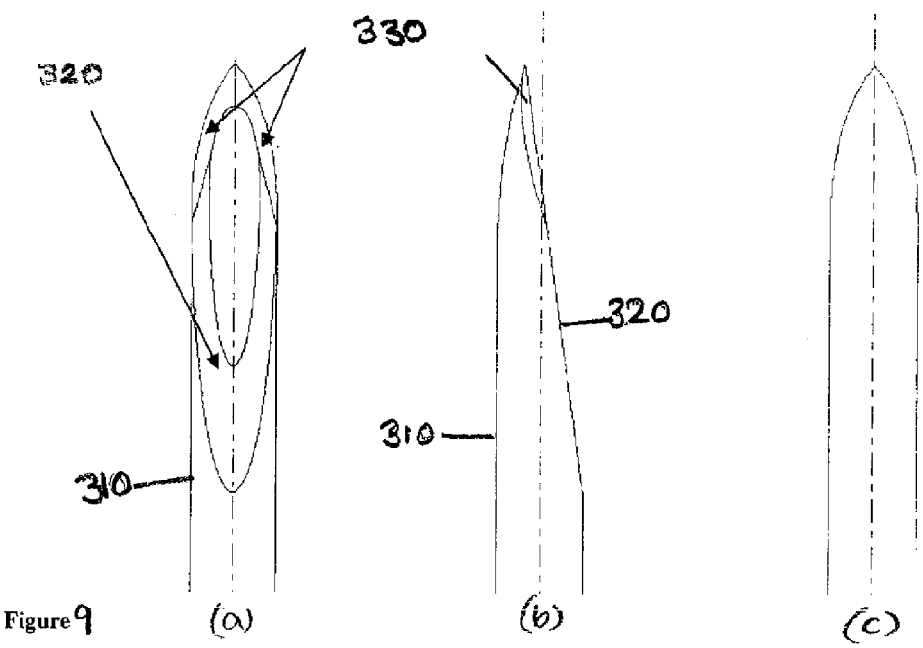
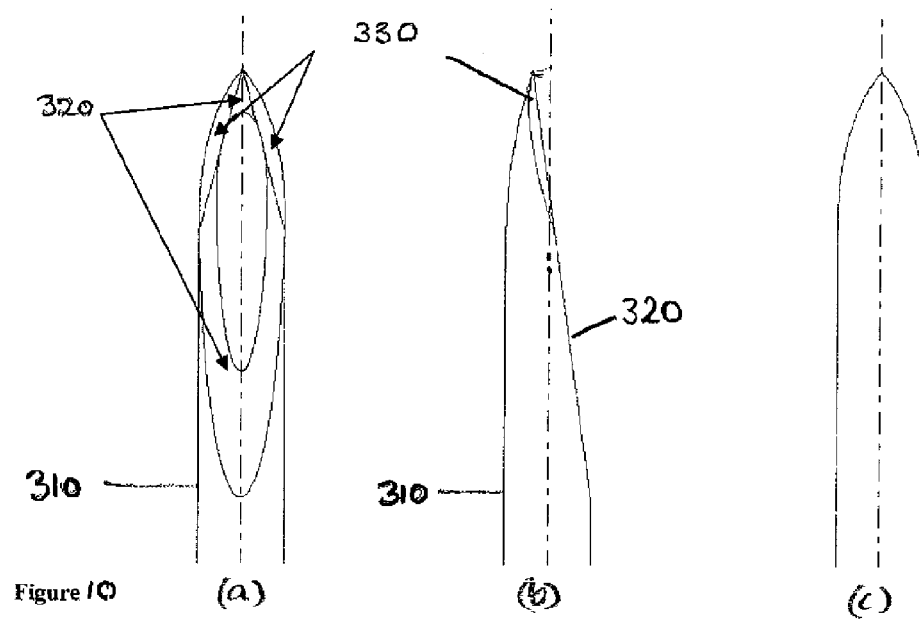

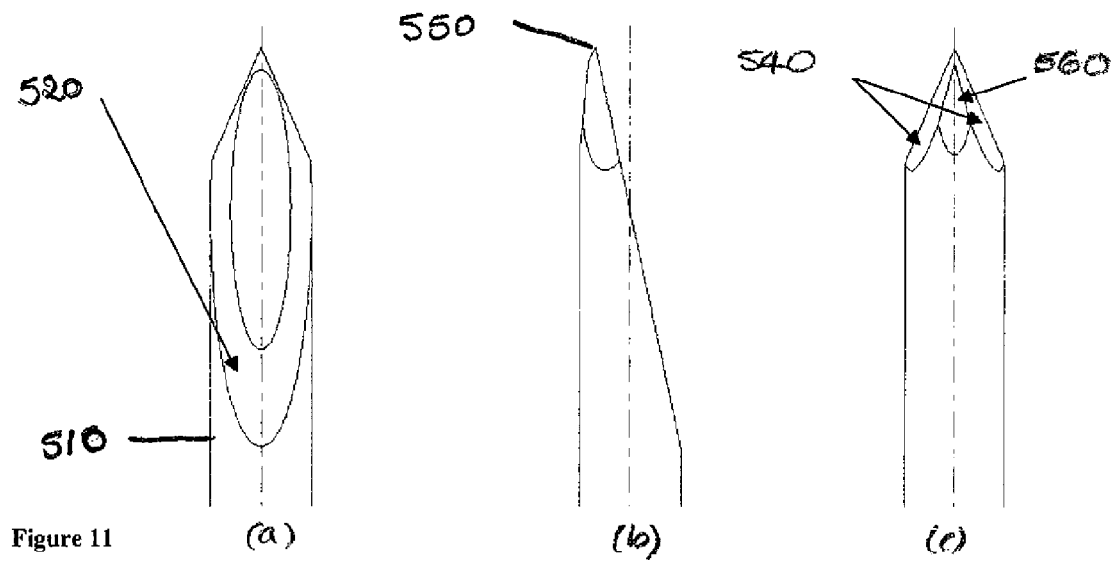
Figure 11 (a) (b) (c)

ND SPECIAL NEEDLE FOR MAKING AN INJECTION AT A PREDETERMINED DEPTH IN THE SKIN

INJECTION APPARATUS AND SPECIAL NEEDLE FOR MAKING AN INJECTION AT A PREDETERMINED DEPTH IN THE SKIN

This application is the U.S. national phase of International Application No. PCT/EP2008/060664 filed 14 Aug. 2008 which designated the U.S. and claims priority to GB Application No. 0716159.9 filed 17 Aug. 2007, the entire contents of each of which are hereby incorporated by reference.

The present invention relates to an injection apparatus and to a method of injection.

Cutaneous injection is used in a number of applications. It is advantageous to inject vaccines into the skin as antigen which is then released into other tissues over a period of time, promoting the response by antibodies and T-cells. Assay sensors may also be injected into the skin, where they can be interrogated optically through the skin. Such assays are described for example in WO 00/02048 and WO 02/30275. They may in particular be useful for glucose monitoring in diabetes. Cutaneous injection is also used cosmetically in wrinkle filling.

The depth at which material is injected is important, as it determines the layer of the skin in which the material will be deposited. The skin consists of two principal layers: the epidermis (upper layer) and the dermis (lower layer), with an overall thickness of 1.5 to 2 mm. The epidermis is overlaid by the stratum corneum, a layer of dead cells approximately 10 to 25 μm thick. The upper cells of the stratum corneum are continuously worn away. The epidermis and dermis are separated by the basement membrane at a depth of approximately 150 μm. The cells at the top of the epidermis progressively die and form the base of the stratum corneum, whilst the basement membrane generates new cells at the base of the epidermis. The dermis is vasculised, whereas the epidermis is not.

The fluorophores commonly used in the competition assays referred to above are illuminated transdermally with blue or green light, which has a low penetration depth. Melanin, which absorbs UV and visible radiation, is produced by the basement membrane and transferred upwards into the epidermis to protect the skin from UV radiation. This melanin absorbs blue and green illumination used to interrogate the sensors and the resulting fluorescence, and accordingly penetration through the skin is poor. Scattering in the skin and absorption of light by blood contributes to this effect. Therefore, the deeper the sensors are positioned in the skin, the weaker the fluorescence detection will be. Accordingly, for optimum sensitivity of the assay, the sensors should be as close to the skin surface as possible.

However, there are disadvantages associated with positioning the reagent particles within the epidermis or basement membrane. In particular, the concentrations of glucose within these layers may not correlate with the blood glucose concentration which the assay is attempting to measure. This is because the epidermis is not vasculised, and the basement membrane uses glucose in the production of epidermal cells which affects its glucose concentration. By contrast, the concentration of glucose in the interstitial fluid of the dermis is expected to correlate with blood glucose concentration. Further, if the reagent particles were positioned in the epidermis, they would move towards the skin surface as the epidermal cells were renewed. Glucose concentration in the epidermis is known to decrease towards the skin surface (and is zero at the stratum corneum). This will lead to an erroneous glucose estimate. Particles injected into the dermis, on the other hand, will be retained permanently, as seen in a conventional tattoo.

In the light of these considerations, the optimum location for assay reagent particles is directly underneath the basement membrane, at the top of the dermis.

In other assays, it may be desirable for sensor particles to be deposited in the epidermis so that they will be expelled from the body over time (WO 02/30275). Shallow injection may be achieved using an array of short needles coated with material to be injected. However, when injection is carried out with an array of this type material is deposited at every depth from the skin surface to the maximum penetration depth of the needle.

An apparatus or method that provides injection to a pre-determined depth is consequently desirable.

An apparatus and method for injection at a desired distance below the surface of the skin are described in WO03/072172. This document describes an injection apparatus having a skin positioning member which lies or is moveable to lie above or below the surrounding area of skin, and means for inserting a needle parallel to the skin positioning member.

International standard nomenclature for needle point geometry is described in ISO7864.

Injection needle types such as a lancet type or trocar type needle are known. Examples of such injection needle types are shown in FIGS. 1 and 2. An injection needle is generally formed from tubing having a lumen (315) and a shaft (310), and a point (325) is formed at the distal end of the needle by cutting across the tubing transversely to its longitudinal axis (305) to form at least one bevel. A lancet type needle (FIG. 1) is formed by making a primary bevel 320 at an angle α to the longitudinal axis 305 then making secondary bevels (330) by increasing the grinding angle α and rotating the needle with respect to the grinding stone about the longitudinal axis of the needle. The two secondary bevels are formed with equal and opposite rotations of the needle about its longitudinal axis with respect to the grinding stone. The rotation angles used for the secondary bevels may be altered depending on the intended use of the needle and are less than 90° with respect to the primary bevel. Typically the rotation with respect to the primary bevel is 55°. A trocar type needle (FIG. 2) may be formed by making three grindings to the needle; the first forms the primary bevel (420), as described above, and the secondary bevels (440) are formed at a 120° rotational angle to each other and to the primary bevel. Furthermore, the grinding angle with respect to the longitudinal axis of the secondary bevels is steeper than the grinding angle α for the primary bevel. The secondary bevels may result in a tip being formed at a position (450) along the radius of the cross-section of the needle perpendicular to the longitudinal axis which lies between the outside of the lumen and the outside of the shaft.

The angles of the primary bevel and of the secondary bevels (if any) with respect to the longitudinal axis together determine the length of the point of the needle, which is defined as the length 325 from the very tip of the needle to the heel (the edge formed by the bevel surface meeting the outer surface of the shaft on the opposite side from the tip; 335).

In a first aspect, the present invention provides an injection apparatus for making an injection at a predetermined depth in skin comprising:

a skin positioning member for positioning on a patch of skin within an area of skin to hold the patch of skin in a defined position, an injection needle comprising a point having a tip at a distal end thereof and a shaft portion immediately proximal to said point, the shaft portion having a longitudinal axis, and means guiding said injection needle for movement from a parking position above the skin beside said skin positioning member to slide beneath said skin positioning member to an injection position in which the distal end of the needle lies at a predetermined distance below said skin positioning member;

wherein:

the tip of the injection needle is closer to the longitudinal axis of the shaft portion than is the outside of the shaft portion.

We have found that, in a device as described in WO03/072172, it is sometimes difficult to insert the needle to the correct depth in the skin due to the shape of the point of the needle. This is particularly found to be a problem with needles having a larger diameter, such as those used for injecting sensor particles as described above. The diameter of needles for such applications may be large compared with the thickness of the skin (1.5 mm). Referring to FIG. 3, using a conventional lancet-type point needle (300), the sensor (360) may be injected too deeply when using the needle with the primary bevel facing away from the skin surface (370) (FIG. 3*b*), or the needle may slide over the skin without penetrating the surface when using the needle with the primary bevel facing towards the skin surface (370) (FIG. 3*a*). It is therefore necessary to solve this problem in order to ensure that a needle may reliably be inserted to the required depth in the skin.

From the description of the known lancet and trocar type needles, it may be seen that known patterns of grinding in some cases do and in some cases do not result in the needle tip being closer to the axis of the lumen than is the outside wall of the surface of the needle. Where the grinding does not provide this feature, we have found that modification of the needle point in order that the tip of the injection needle is closer to the longitudinal axis of the shaft portion than is the outside of the shaft portion allows for more reliable insertion of the needle to the required depth in skin.

Suitably, the needle tip may be made closer to the longitudinal axis of the shaft portion than is the outside of the shaft portion by modifying a lancet-type needle of the type described above by bending the tip of the needle towards the longitudinal axis of the shaft. Suitably, the bending of the tip of the needle may be done before or after the formation of the secondary bevels of the point are carried out. Preferably, however, the bending of the tip is carried out before the secondary bevels are formed in order to avoid producing a sharp edge at the tip of the needle that may damage the sensor to be injected.

Alternatively, the needle tip may be made closer to the longitudinal axis of the shaft portion than is the outside of the shaft portion by providing a suitable grinding or combination of grindings at the needle tip. Suitably, a trocar-type needle of the type described above may be used. Such a trocar-type needle may be provided with at least one further grinding at the tip of the needle which, without changing the position of the needle tip relative to the longitudinal axis of the needle, provides a more gradual slope from the outside of the shaft towards the tip on the back of the needle (the side opposite the heel).

The inventors have proposed that the incorrect positioning of the injected material resulting from using the needle with the primary bevel facing away from the surface of the skin (as in FIG. 3*b*) may be due to bending of the needle during insertion into the skin caused by a component of the reaction force from the skin acting on at least the primary bevel perpendicular to the injection path. This bending results in deviation of the needle from the intended injection path.

When injecting material such as a solid sensor particle, it is particularly important that the injection is made at the correct depth to ensure correct placement of the sensor in the skin, and a large gauge needle must be used in order to accommodate the sensor within the lumen. Thus, the inventors have devised a needle in which the component of the reaction force acting perpendicular to the injection path is reduced compared with standard designs of injection needle.

Accordingly, the present invention provides in a second aspect an injection apparatus for making an injection at a predetermined depth in skin comprising:

a skin positioning member for positioning on a patch of skin within an area of skin to hold the patch of skin in a defined position, an injection needle comprising a tip, at least one bevel and a heel together forming a point at a distal end thereof, and a shaft portion immediately proximal of said heel having a longitudinal axis, including a lumen extending along the longitudinal axis, wherein the at least one bevel is formed between said tip and said heel such that a lumen opening is defined extending from the tip to a proximal end of the lumen opening located distal of the heel; and means guiding said injection needle for movement from a parking position above the skin beside said skin positioning member to slide beneath said skin positioning member to an injection position in which the distal end of the needle lies at a predetermined distance below said skin positioning member;

wherein:

the length of the lumen opening of the needle is in a range from 5 to 15 times the diameter of the shaft of the needle. For example, the length of the lumen opening of the needle may be in the range from 8 to 12 times the diameter of the shaft of the needle, such as ten times the diameter of the shaft of the needle.

The present invention further provides in a third aspect an injection needle comprising a tip, at least one bevel and a heel together forming a point at a distal end thereof, and a shaft portion immediately proximal of said heel having a longitudinal axis, including a lumen extending along the longitudinal axis, wherein the at least one bevel is formed between said tip and said heel such that the lumen opening is defined from the tip to a proximal end of the lumen opening located distal of the heel, characterised in that the length of the lumen opening of the needle is in a range from 5 to 15 times the diameter of the shaft of the needle. For example, the length of the lumen opening of the needle may be in the range from 8 to 12 times the diameter of the shaft of the needle, such as ten times the diameter of the shaft of the needle.

Preferably, the needles of the second and third aspects of the invention have a shaft diameter of from 0.5 mm to 1.5 mm, for example 0.8 to 1.3 mm or 1.0 to 1.2 mm, particularly preferably 1.1 mm. Where the shaft diameter is 1.1 mm, the length of the lumen opening may be from 5.5 mm to 16.5 mm, for example 8.8 to 13.2 mm, such as 11 mm.

Preferably, at least a part of the point of a needle of the second or third aspect of the invention is formed substantially parallel to the longitudinal axis of the needle, and most preferably, at least half of the point length is formed parallel to the longitudinal axis of the needle. This results in that part of the point having a part-cylindrical form with a constant cross-section. Preferably, the distance perpendicular to the longitudinal axis of the needle from the tip to the bevel face at the part-cylindrical point section is at least 50% of the diameter of the shaft of the needle, such as 60% or 70%. Preferably, the part-cylinder has a semi-circular cross-section, i.e. is a hemi-cylinder. Preferably, the section of the point distal of the part-cylindrical point section is shaped into a desired needle tip geometry, suitably a lancet or trocar tip geometry, and that geometry may suitably be modified in accordance with the needles described in the first aspect of the invention. Preferably, the section of the point immediately distal of the heel and proximal of the part-cylindrical point section forms a further bevel at an angle to the longitudinal axis, suitably 8 to 12°, such as 10°. Suitably, the transition between the part-cylindrical point section and the further bevel may be a rounded transition or a chamfered transition.

Suitably, the needle tip may be bent or ground or otherwise shaped such that the tip is closer to the longitudinal axis of the needle, as described previously.

An additional benefit of using a needle according to the second or third aspect of the invention is that, when using needles having an outer diameter that is a significant proportion of the thickness of the dermis (around 1.5 mm) for intradermal injection, there is a reduction of the stress and lesions in the dermis caused by the insertion of the needle compared with that caused by a conventional needle. The stress and lesions may be further reduced if the full diameter of the needle tube is introduced only a short distance, such as 1 mm, into the skin.

Preferably, the apparatus further comprises means for attaching said skin positioning member to the skin.

Preferably, said skin positioning member is arranged such that at least a portion of said skin positioning member lies or is moveable to lie above or below said area of skin such that at least a part of said patch of skin is held elevated above or depressed below said area of skin.

Preferably, the needle is guided for movement of the distal end of the needle at a constant distance below the surface of a lifted patch of skin attached to the skin positioning member. This will ensure that the injection depth is not dependent on the precise distance over which the needle point is moved, as would be the case if the needle moved obliquely with respect to the skin positioning member. Preferably, the skin positioning member holds the surface of the lifted area of skin flat (planar). The movement of the needle is then preferably parallel to the skin positioning member surface.

The skin positioning member preferably has adhesive thereon to secure the patch of skin to the skin positioning member. Alternatively, the skin positioning member may be porous or provided with bores through which vacuum may be applied to hold the skin to the skin positioning member. In an alternative embodiment, the skin positioning member may be pressed against the patch of skin to depress the patch of skin. Such depression of the patch of skin may be such that the patch of skin lies obliquely slanted with respect to the natural orientation, allowing the needle to penetrate therebelow from its edge.

The skin positioning member may be plate-like, or may form the surface of a non-plate-like member, for example a cone, a pyramid, a triangular prism or a hemisphere.

Preferably, said skin positioning member is moveable between a first position in which it lies on said area of skin and a second position in which at least a portion of said skin positioning member is elevated above or depressed below said area of skin with said patch of skin. However, the skin positioning member may be fixed in a position elevated above the surface of the skin and the skin may be drawn up to the skin positioning member by the application of vacuum and retained there against the skin positioning member by vacuum or by adhesive as described, or the skin positioning member may be fixed in a position depressed below said area of skin.

Preferably, means are provided for tilting said skin positioning member to elevate an edge thereof with said patch of skin attached thereto to lift said patch of skin. Alternatively, however, the whole skin positioning member may be elevated, with or without some tilting also, to raise the patch of skin. To conveniently provide for the tilting movement, said skin positioning member is preferably carried by a support structure to which the skin positioning member may be hinged at one edge of the skin positioning member.

The skin positioning member may be moved using by the interaction of one or more cam followers carried by the skin positioning member each engaging a cam groove in a cam plate which is mounted for sliding movement with respect to the skin positioning member.

The injection needle preferably is guided for movement using one or more cam followers attached to the needle each engaging in a cam groove in a cam plate mounted for sliding movement with respect to the needle and the same cam plate may control the movement of the skin positioning member and of the injection needle.

The apparatus may comprise a lower portion which is left on the skin after injection to define or mark the injection site and an upper portion containing the injection needle which is detachable after injection. Said upper portion may further include said skin positioning member although this could be mounted to the lower portion so that it is left behind when the upper portion is removed. It could then either remain as part of the lower portion or be removed separately. If it were made transparent, it could remain covering the injection site and optical interrogation of an injected sensor could be made therethrough.

The predetermined depth at which injection is made using the apparatus is suitably in the range of 100 µm to 2 mm and may be fixed during manufacture or may be user adjustable.

Said injection needle is preferably carried by a syringe comprising a chamber for injectable material and means for dispensing said material through said needle. The syringe may contain as said injectable material particles to be injected and may contain in separate compartments said particles to be injected and a liquid for suspending the particles.

As indicated above, desirably the particles are assay sensor particles containing assay reagents. However, the injectable material in the syringe may alternatively be a medicament and may be an antigen for use in an immunisation. The injectable material may be in the form of a liquid, paste, emulsion, a single implant or sensor particle, a plurality of implants or sensor particles, or a suspension of implants or sensor particles in a liquid.

The invention includes in a fourth aspect injection apparatus comprising a housing containing an injection needle comprising a point having a tip at a distal end thereof and a shaft portion immediately proximal to said point having a longitudinal axis and mounted for guided movement from a parked position to an operative position, a detachable marker unit mounted to said housing and so positioned that said needle passes therethrough to reach said operative position, and means for securing said marker unit at an injection site prior to the making of an injection, wherein said tip of the injection needle is closer to the longitudinal axis of the shaft portion than is the outside of the shaft portion of the needle, and whereby said apparatus can in use be positioned at an injection site, said marker unit can be secured at said injection site, said needle can be moved to said operative position to make an injection and said housing can be removed leaving said marker unit at the injection site to mark the position thereof.

Said marker unit may comprise a plate having an aperture therein through which the needle passes in use. Said aperture preferably has a maximum dimension of 2 mm or less. Apparatus according to this fourth aspect of the invention may have all or any of the features described above in connection with the first aspect of the invention.

In a fifth aspect, the present invention provides an injection apparatus comprising a housing containing:

an injection needle comprising a tip, at least one bevel and a heel together forming a point at a distal end thereof, and a shaft portion immediately proximal of said heel having a longitudinal axis, including a lumen extending along the longitudinal axis, wherein the at least one bevel is formed between said tip and said heel such that a lumen opening is defined from the tip to a proximal end of the lumen opening located distal of the heel, said injection needle being mounted for guided movement from a parked position to an operative position;

a detachable marker unit mounted to said housing and so positioned that said needle passes therethrough to reach said operative position; and means for securing said marker unit at an injection site prior to the making of an injection; wherein the length of the lumen opening of the needle is in a range from 5 to 15 times the diameter of the shaft of the needle, and whereby said apparatus can in use be positioned at an injection site, said marker unit can be secured at said injection site, said needle can be moved to said operative position to make an injection and said housing can be removed leaving said marker unit at the injection site to mark the position thereof.

Said marker unit may comprise a plate having an aperture therein through which the needle passes in use. Said aperture preferably has a maximum dimension of 2 mm or less. Apparatus according to the fourth and fifth aspects of the invention may have all or any of the features described above in connection with the first, second or third aspects of the invention.

The invention further includes a method of fixed-depth cutaneous injection comprising: holding the surface of a patch of skin in a defined position against the surface of a skin positioning member and guiding an injection needle beneath the skin positioning member to bring a discharge opening of the injection needle to a predefined location beneath the skin positioning member, wherein the injection needle comprises a point having a tip at a distal end thereof and a shaft portion immediately proximal to said point having a longitudinal axis, and wherein the tip of the needle is closer to the longitudinal axis of the shaft portion than is the outside of the shaft portion. This method may be carried out using apparatus according to either or both of the first and fourth aspects of the invention.

The invention includes a second method of fixed-depth cutaneous injection comprising: holding the surface of a patch of skin in a defined position against the surface of a skin positioning member and guiding an injection needle beneath the skin positioning member to bring a discharge opening of the injection needle to a predefined location beneath the skin positioning member, wherein the injection needle comprises a tip, at least one bevel and a heel together forming a point at a distal end thereof, and a shaft portion immediately proximal of said heel having a longitudinal axis, including a lumen extending along the longitudinal axis, wherein the at least one bevel is formed between said tip and said heel such that the lumen opening is defined from the tip to a proximal end of the lumen opening located distal of the heel, and wherein the length of the lumen opening of the needle is in a range from 5 to 15 times the diameter of the shaft of the needle. This method may be carried out using apparatus according to either or both of the second and fifth aspects of the invention.

Suitably, these methods can be carried out by a patient on himself/herself without the need for assistance from medical personnel.

Preferably, said injection needle is guided such that not more than 1 mm of the length of the shaft portion of the needle is inserted beneath the surface of the skin.

The invention will be further described with reference to the preferred embodiments shown in the accompanying drawings, in which:

FIG. 6 shows the same perspective view but with some upper components removed;

FIG. 10 shows another example of a needle for use in the apparatus of the present invention. View (a) shows the primary bevel face of the needle, view (b) shows the needle rotated by 90° about its longitudinal axis compared with view (a), and view (c) shows the needle rotated about its longitudinal axis by 180° compared with view (a).

FIG. 11 shows another example of a needle for use in the apparatus of the present invention. View (a) shows the primary bevel face of the needle, view (b) shows the needle rotated by 90° about its longitudinal axis compared with view (a), and view (c) shows the needle rotated about its longitudinal axis by 180° compared with view (a).

Figure 4:
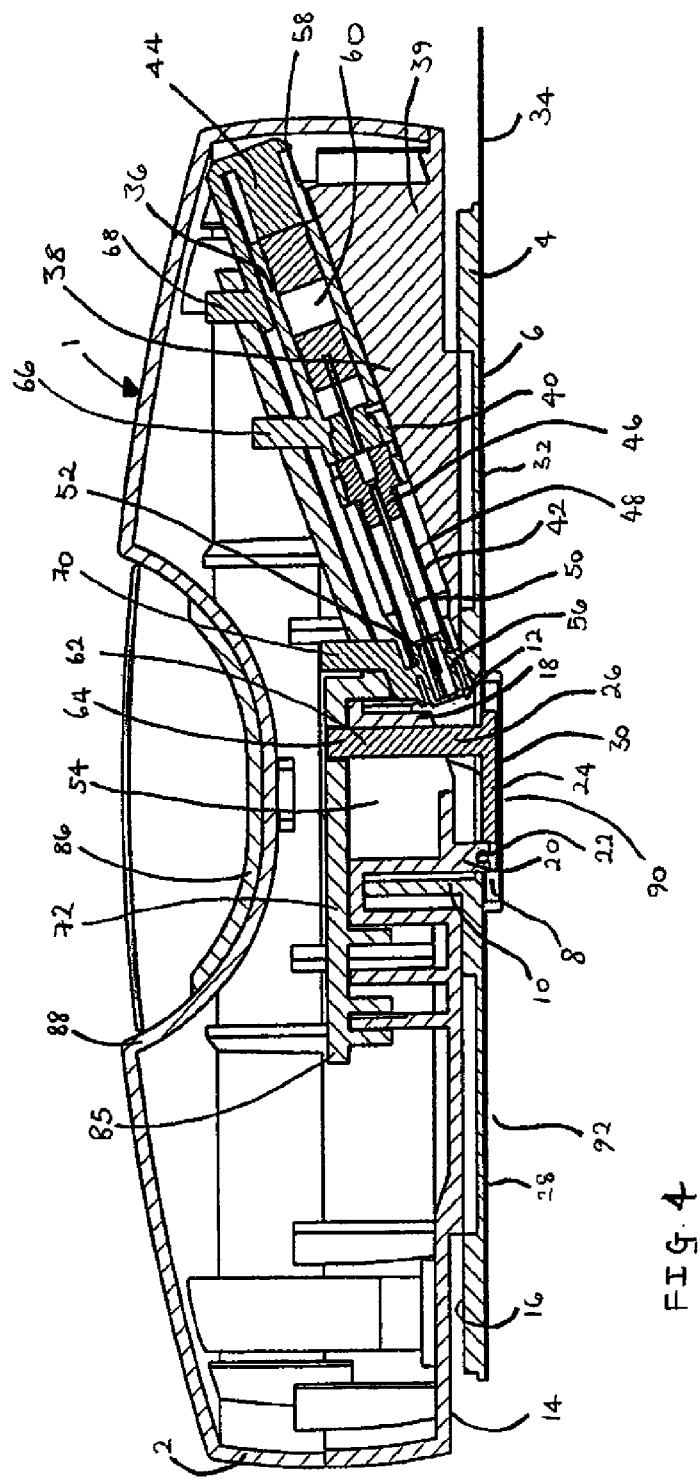
FIG. 4 shows a vertical cross section through an illustrative embodiment of the invention.
Figure 5:
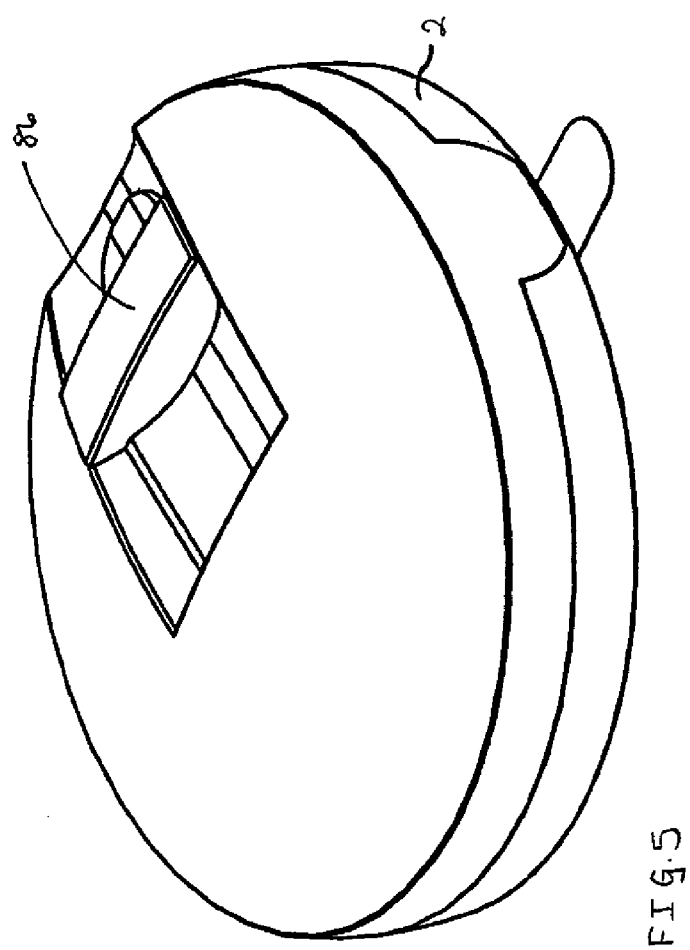
FIG. 5 shows the same embodiment in perspective view.

In a first variant of the injection apparatus according 30 to the present invention, as shown in FIG. 4, the injection apparatus 1 comprises an upper portion 2 and a lower portion 4. The lower portion may constitute or include a marker unit in certain example embodiments. The lower portion comprises a circular plate 6 having a central hole 8 defined by a cylindrical boss 10 with an aperture 12. The upper portion 2 is dome-shaped, and has a lower surface 14 which lies on the upper surface 16 of the lower portion 4. The upper portion 2 has a central cylindrical boss 18 extending downwards inside the boss 10 of the lower portion 4. The rim 20 of the upper portion boss 18 is attached by a pivot 22 to a skin positioning member constituted by a base plate 24 of a bell crank 26. The base plate 24 occupies the central hole 8 of the lower portion 4. The lower surface 28 of the lower portion 4 and the lower surface 30 of the base plate 24 have an adhesive covering 32, 10 which is covered with a release tape 34.

The upper portion 2 comprises a syringe 36 mounted in a cylindrical sleeve 38 at an angle of approximately 20° to the lower surface 14 of the upper portion 2. The sleeve 38 forms an integral part of a wedge shaped block 39. The sleeve 38 has an axial slot 41 on its upper surface. The syringe 36 comprises a syringe body 40, a needle housing 42 and a plunger 44. The needle housing 42 extends from the lower end 46 of the syringe body 40, and comprises a collapsible sleeve 48 housing a needle 50 which is attached to the syringe body 40. At its distal end 52 the needle housing 42 passes through the aperture 12 and lies inside a chamber 54 defined by the lower portion boss 10, and is sealed with an end cap 56. The plunger 44 lies in the upper end 58 of the syringe body 40. The syringe body 40 contains material to be injected. In an alternative variant, the double chamber syringes described below may be used.

The upper portion 62 of the bell crank 26 forms a cam follower 64. Cam followers 66, 68, 70 are also mounted on the syringe body, the syringe plunger and the end cap respectively and protrude through the slot 41 in the sleeve 38. Each of the cam followers 64, 66, 68, 70 is constrained to radial movement in the direction 71.

A grooved cam plate 72 engages the cam followers 64, 66, 68, 70 to form a box cam. A cam groove 74 engaging cam follower 64 is initially angled to the left and then runs straight outwards towards the periphery of the apparatus 1. Cam grooves 76, 78 engaging cam followers 66, 68 initially run parallel to the final portion of the cam groove 74, then are angled to the left with the cam groove 78 engaging cam follower 68 more steeply angled, then parallel to the final portion of the cam groove 74. A cam groove 80 engaging cam follower 70 runs parallel to the final portion of the cam groove 74. The cam grooves 76, 78, 80 engaging cam followers 66, 68, 70 terminate in a common lateral cam groove 82 which is perpendicular to the final portions of the cam grooves 76, 78, 80. A spring (not shown) urges the cam followers 66, 68, 70 to the right. The cam plate 72 is mounted on runners 84 such that it is constrained to slide forwards and backwards in the direction 85 only. The cam plate 72 is attached on its upper surface 73 to a boss 87 which engages a manually engageable slider 86 on the upper surface 88 of the upper portion 2.

In use, the release tape 34 is removed from the adhesive covering 32 of the lower portion lower surface 28 and the bell crank base plate lower surface 30. The adhesive lower surface 28, 30 is applied to the skin. A small area of skin 90 becomes adhesively attached to the bell crank base plate 24, and an annular area of skin 92 surrounding the small area of skin 90 becomes adhesively attached to the lower portion 4.

To effect injection, the manually engageable slider 86 is pushed across the upper surface 88 of the upper portion 2 by the user. This causes the cam plate 72 to move forward along the runners 84 from its initial position shown in FIG. 6 to a final position. As the cam plate 72 moves, the cam follower 64 of the bell crank 26 is immediately moved to the left by the cam groove 74. This causes the bell crank 26 to rotate around the pivot 22, such that the base plate 24 of the bell crank 26 and the adhesively attached small area of skin 90 tilt relative to the lower surface 28 of the lower portion 4 to an angle of approximately 20°.

As the plate 72 continues to move forward, the cam follower 66 on the syringe body 40 is moved to the left by its cam groove 76. This causes the syringe needle 50 to move through the end cap 56 and into the chamber 54 defined by the lower portion boss 10, collapsing the needle housing 42. The needle 50 extends parallel to the lower surface 30 of the bell crank base plate 24 at a defined distance from it, such that it extends under the small area of skin 90 parallel to the skin surface at a defined depth. The depth may for example be 100 μm, which lies in the dermis just below the junction with the epidermis. In an alternative embodiment, the distance between the bell crank base plate 24 and the needle 50 (and hence the depth of injection) may not be preset in manufacture but may be set by the user within a certain range, for example using a dial coupled to a screw jack lifting the needle assembly.

Simultaneously, the cam follower 68 on the syringe plunger is moved to the left by its cam groove 78. The steeper angle of this cam groove 78 compared with the cam groove 76 for cam follower 66 means that the syringe plunger 44 moves to the left relative to the syringe body 40 and travels down the syringe body 40. This causes the material 60 to be injected to be expelled through the needle 50 into the skin.

When the plate 72 reaches its final position, the cam followers 66, 68, 70 are forced to the right in the lateral groove 80 by the spring (not shown), retracting the syringe 36 into its sleeve 38. The syringe 36 is now shorter in length because the needle housing 42 has collapsed, and therefore the syringe 36 does not protrude into the chamber 54 defined by the boss 10. The upper portion 2 of the injection apparatus 1 can thus be removed from the skin surface. It is necessary to remove the adhesive coating 32 from the lower surface 30 of the bell crank base plate 24 to achieve this.

The lower portion 4 of the injection apparatus 1 is left adhesively attached to the annular area of skin 92. Its central hole 8 is used to define the site of injection. This may be important, for example in the injection of assays which need to be interrogated optically or otherwise at the site of injection.

Figure 9:
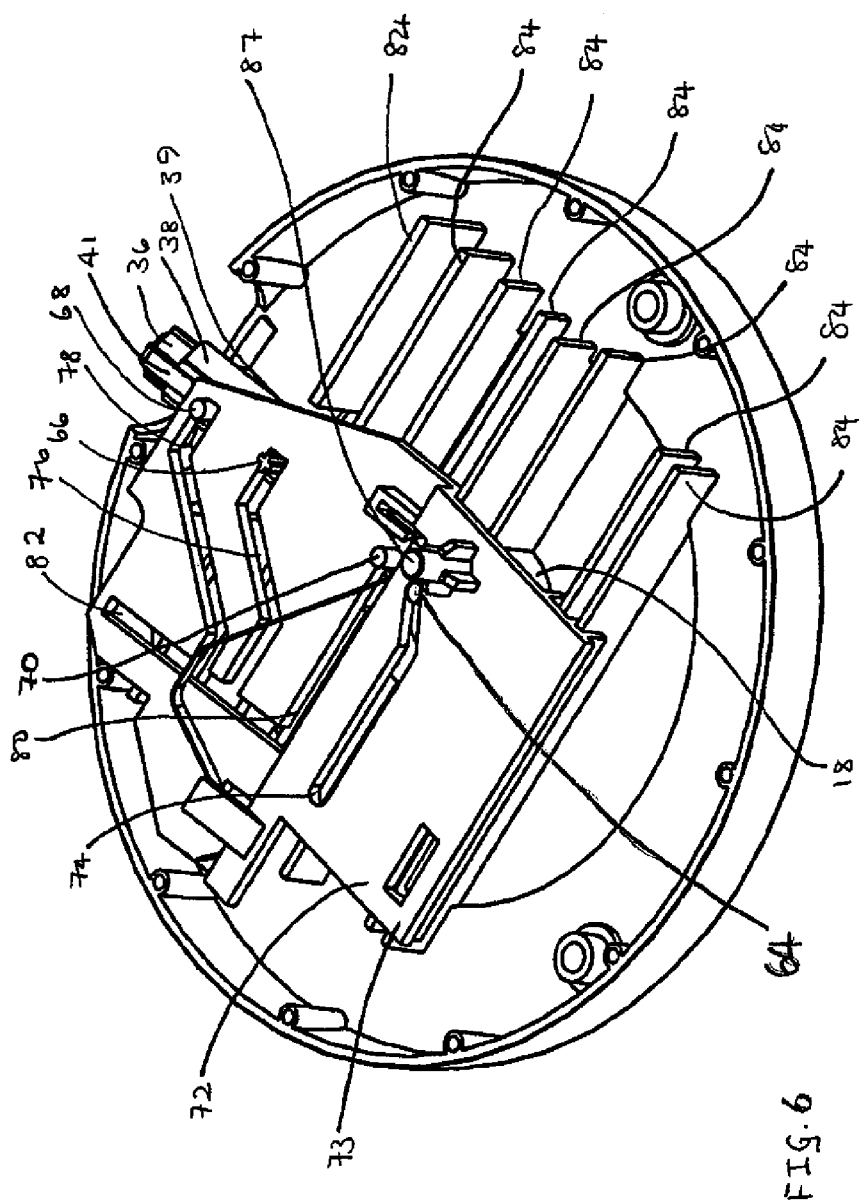
FIG. 9 shows an example of a needle for use in the apparatus of the present invention. View (a) shows the primary bevel face of the needle, view (b) shows the needle rotated by 90° about its longitudinal axis compared with view (a), and view (c) shows the needle rotated about its longitudinal axis by 180° compared with view (a).

The needle for use in the above-described injection apparatus, in accordance with the first and fourth aspects of the invention, has a tip which is closer to the longitudinal axis of the needle than is the outside of the shaft of the needle. One way of achieving this is to bend the needle tip towards the longitudinal axis of the needle. Such a needle is commercially available as a Huber tip needle, for example from www.harvardapparatus.com. The bent needle may also be provided with suitable shaping at the point. For example, as shown in FIG. 9, the needle 310 may be of the form of a lancet-type needle, having a primary bevel face 320 and secondary bevels 330 formed at equal and opposite rotational angles about the longitudinal axis of the needle. The shaping may be provided by any conventional means, such as grinding of the needle with an abrasive surface such as a whetstone. The tip of the needle may be bent towards the longitudinal axis after the secondary bevels have been formed, as shown in FIG. 9. Alternatively, the tip may be bent before the secondary bevels are formed, as shown in FIG. 10.

Figure 2:
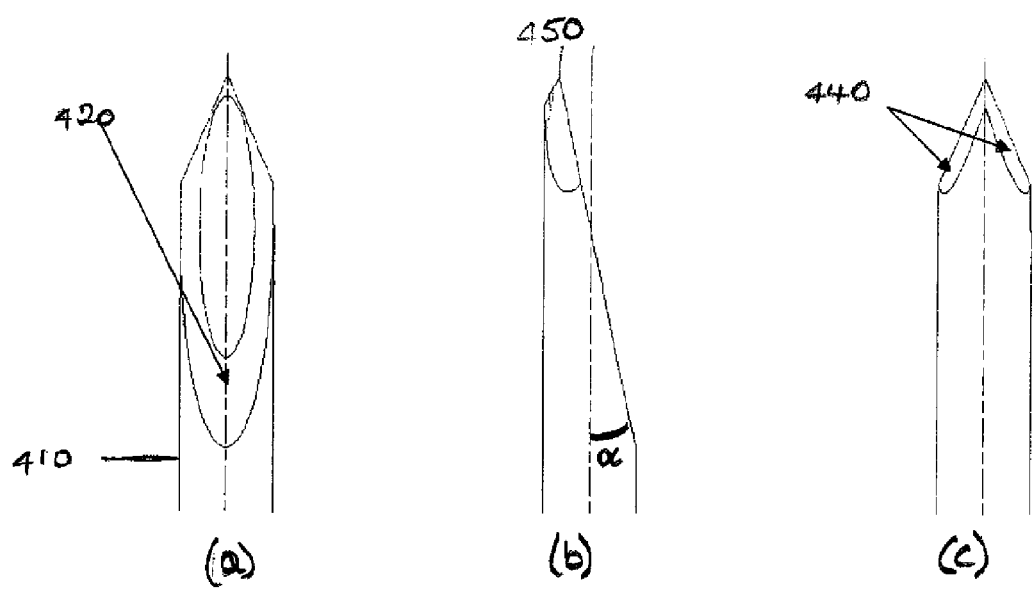
FIG. 2 shows an example of a needle for use in the apparatus of the present invention. View (a) shows the primary bevel face of the needle, view (b) shows the needle rotated by 90° about its longitudinal axis compared with view (a), and view (c) shows the needle rotated about its longitudinal axis by 180° compared with view (a).
Figure 3:
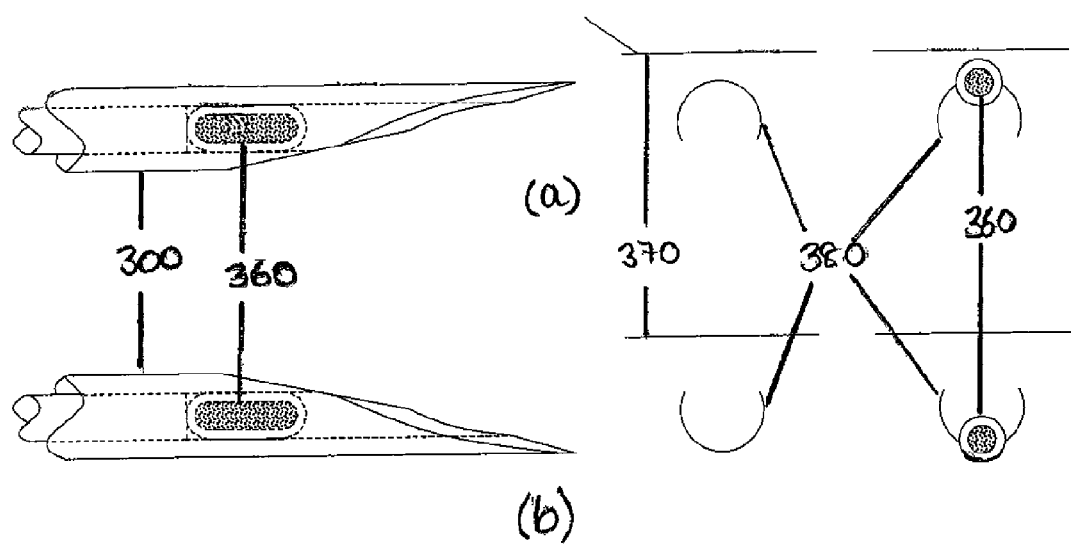
FIG. 3 shows the resulting position of a sensor injected using the primary bevel of the needle (a) facing towards the skin, and (b) facing away from the skin.

A second method of making the needle tip closer to the longitudinal axis than is the outside of the needle shaft is to provide additional shaping of the tip of the needle by suitable means such as grinding with an abrasive surface. The known trocar-type needle is an example of the use of such additional shaping, and the shape of the point of this type of needle tip is shown in FIG. 2. This type of needle has a primary bevel 420, and two secondary bevels 440, each formed at a rotational angle about the longitudinal axis of needle 410 of 120° to each other and to the primary bevel. It is seen from the Figure that the tip 450 of the needle 410 is thus formed closer to the longitudinal axis of the needle than is the outside of the shaft of the needle.

Alternatively or additionally, at least one grinding may be formed at the tip of the needle in order to make the tip closer to the longitudinal axis. For example, a single grinding 560 may be formed at a rotational angle of 180° to the primary bevel 520, which grinding 560 is inclined from the outside of the needle shaft towards the longitudinal axis of the needle.

An additional grinding as described above may be advantageously be added to a trocar needle. While not necessarily resulting in an adjustment of the tip position relative to the longitudinal axis, the additional grinding removes the sharp front edge of the tip of a standard trocar needle that may split the skin surface when the needle is inserted parallel thereto. An example of such a needle is shown in FIG. 11, and is described in U.S. Pat. No. 5,968,022.

An alternative needle type advantageous in the injection methods and apparatuses of the second and fifth aspects of the present invention is a needle according to the third aspect of the invention in which the length of the lumen opening of the needle is in a range from 5 to 15 times the diameter of the shaft of the needle.

The intention in using such a needle is to reduce the asymmetry and apparent gauge of the needle and thereby reduce forces perpendicular to the skin surface during forming of the injection channel. This in turn reduces the propensity of the needle to bend when being inserted into the skin, and thus minimises the deviation of the needle from the intended injection path.

In order to achieve the above, the point of the needle, is formed by further shaping in order to remove part of the needle shaft and expose the lumen of the needle, resulting in a part-cylindrical portion. This shaping also includes the creation of a further bevel immediately distal of the heel of the needle in order to facilitate the expansion of the channel formed by the needle tip to accommodate the diameter of the shaft of the needle. Thus, when the channel has been formed by the part-cylindrical portion of the point, it is then expanded to the full diameter of the needle tube by the insertion of the further bevel in order that the injection of the desired material may be carried out. Two planes at different angles to the longitudinal axis (though at the same rotational angle about the longitudinal axis) may therefore be provided by the further shaping in order to form a stepped bevel face. A graduated transition may be provided between the part-cylindrical section and the further bevel, such as a curved transition, or there may be a sharp angle formed between the part-cylindrical portion and the further bevel.

It is possible to envisage the manufacture of such a needle in a number of ways. For convenience, the description of the manufacture of the needle will be described starting from a lancet needle of known type. However, it will be appreciated that other types of needle, such as a trocar needle or a plain needle with a single bevel and no further shaping of the point, may be used as a suitable starting point, or that the needle point may be shaped into the desired form, such as a trocar or lancet point, after the shaping described below has been carried out. The proximal end of the lumen opening of the needle may additionally be shaped in a known manner, such as by dulling the edge to prevent coring. This needle design may in principle be applied to any size of needle. It is envisaged that such needles for use in intradermal injection will have a shaft diameter in the range of 0.5 to 1.5 mm.

Figure 1:
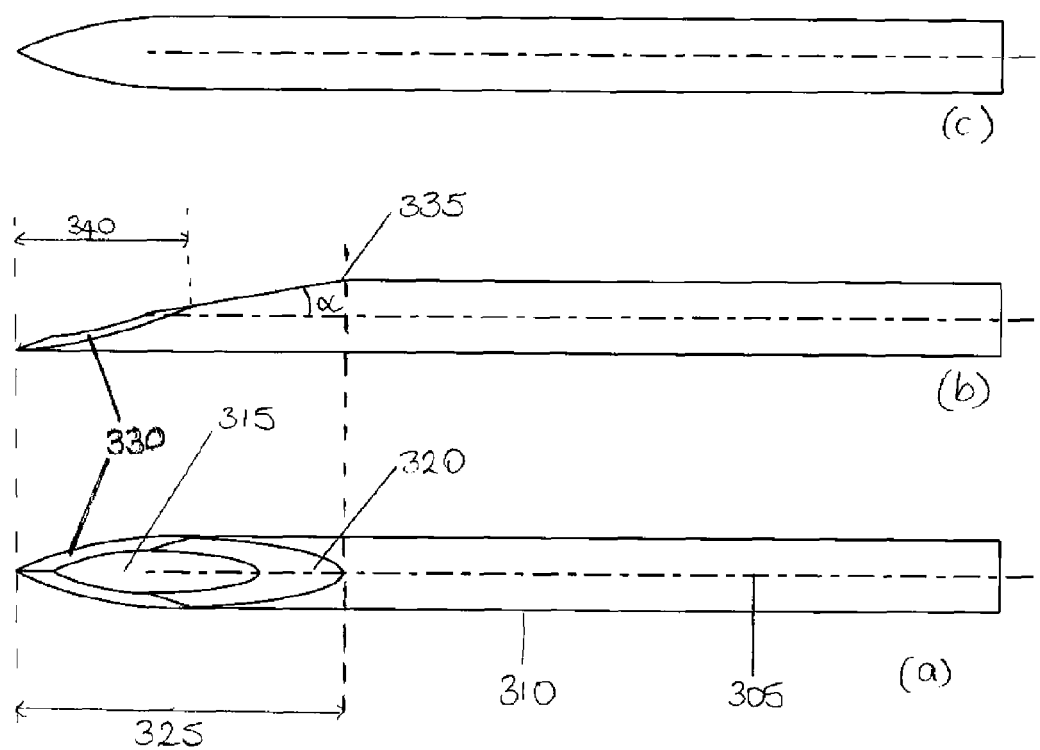
FIG. 1 shows an example of a known lancet-type injection needle. View (a) shows the primary bevel face of the needle, view (b) shows the needle rotated by 90° about its longitudinal axis compared with view (a), and view (c) shows the needle rotated about its longitudinal axis by 180° compared with view (a).
Figure 12:
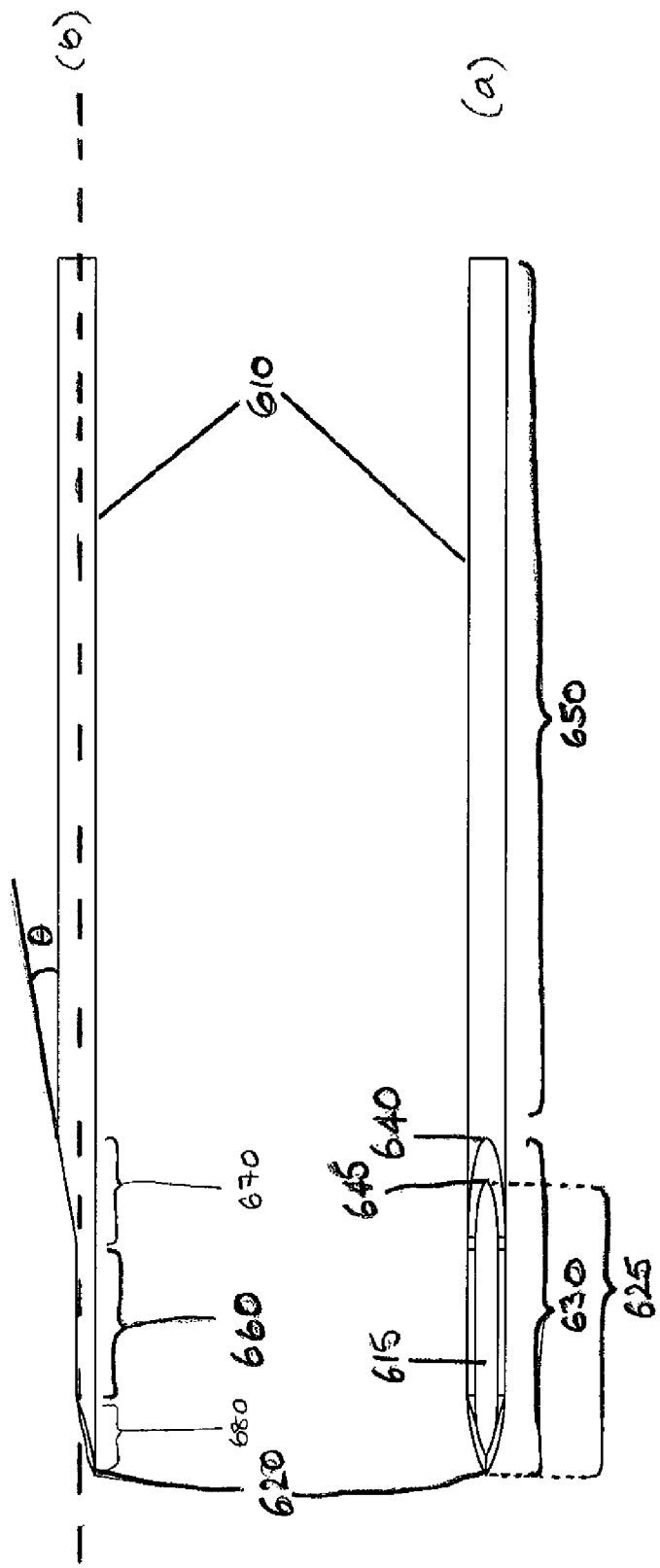
FIG. 12 shows an example of a needle according to the present invention. View (a) shows the primary bevel face of the needle, and view (b) shows the needle rotated by 90° about its longitudinal axis compared with view (a).

Referring to FIG. 12, two depictions of a needle according to the present invention are shown (elevation: FIG. 12(*b*); plan: FIG. 12(*a*)). The needle 610 depicted has a tip 620 shaped as for a known lancet needle, having a primary bevel and two secondary bevels as described above. A standard lancet needle has secondary bevels whose lengths 340 (FIG. 1), 680 (FIG. 12) are in the range from 2 to 2.5 times the diameter of the needle shaft. The point 630 of the needle extends from the tip 620 to the heel 640 and includes the whole of the tip and the heel. The lumen opening 625 extends from the tip 620 to the proximal end of the lumen opening 645, distal of the heel. The length of the lumen opening of the needle may be in the range of from 5 to 15 times the diameter of the needle shaft, for example 8 to 12 times, such as 10 times the diameter of the needle shaft. Thus, for a needle for intradermal injection having a 1.1 mm shaft diameter (19G), the length of the lumen opening may be from 5.5 mm to 16.5 mm, for example 8.8 mm to 13.2 mm, such as 11 mm. The shaft 650 comprises the whole of the needle proximal of the heel. It can be seen that a section of the needle has been removed from point 630, forming a part-cylindrical portion, and exposing the lumen of the needle at 660.

Figure 13:
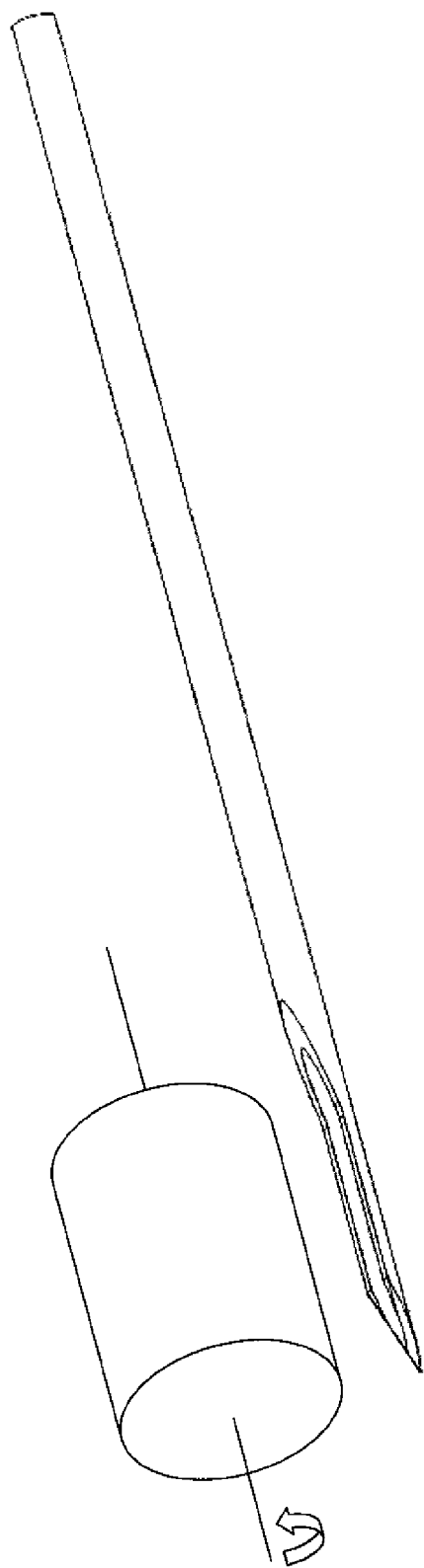
FIG. 13 shows a method of manufacturing a needle according to the present invention.

The shaping of the point at 660 and/or the bevel 670 (proximal of 660 and distal of heel 640) may be achieved by grinding the needle using a rotating grinding stone having its axis of rotation parallel to the longitudinal axis of the needle. Such an arrangement is shown in FIG. 13. Where this method is used, the curvature of the surface of the grinding stone determines the shaping of the needle at the transition between the part-cylindrical portion and the further bevel of the needle. For example, a rounded edge of the grinding stone will result in a rounded transition, whereas a chamfered edge will result in a corresponding chamfered transition.

Figure 14:
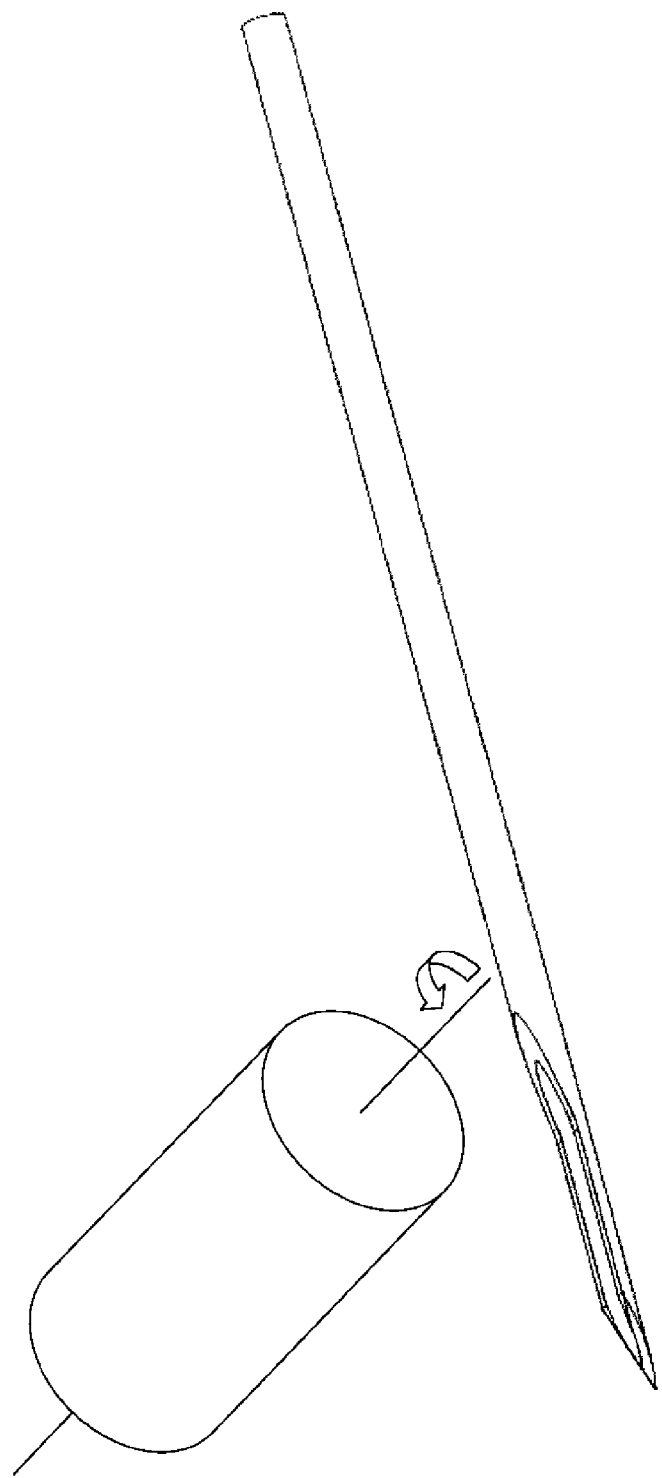
FIG. 14 shows another method of manufacturing a needle according to the present invention.

Alternatively, the shaping of the point at 660 and/or the further bevel 670 may be achieved by grinding the needle using a rotating grinding stone having its axis of rotation perpendicular to the longitudinal axis of the needle. Such an arrangement is shown in FIG. 14. Where this method is used, the diameter of the grinding stone is selected to achieve the required shape of the transition between the part-cylindrical portion and the further bevel 670. The grinding stone may also be used to shape the further bevel 670 to the required angle θ to the longitudinal axis of the needle.

Figure 15:
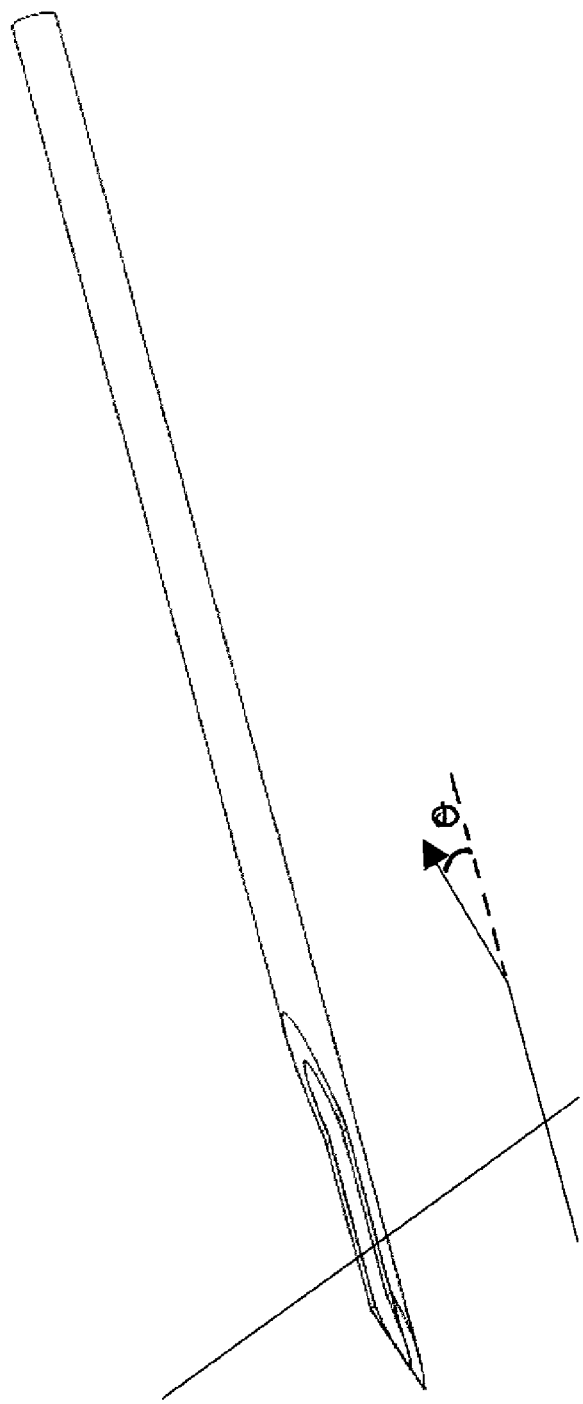
FIG. 15 shows a further method of manufacturing a needle according to the present invention.

As a further alternative, the shaping of the point at 660 and the further bevel 670 may be achieved by wire erosion of the needle. Such an arrangement is depicted in FIG. 15. The shape of the point of the needle is defined by the path cut by the wire through the needle. Suitably, the path of the wire may be substantially in the plane of the longitudinal axis at 660, and at a desired angle θ to the longitudinal axis to form the further bevel 670. At 660 it is envisaged that the wire may be moved in a path at an angle e-x to the longitudinal axis, so that the apparent diameter of the needle increases gradually from the tip towards the heel. Suitably, the angle θ may be 10°, and the angle x may be between 0 and θ, such as 0 to 5°. Preferably, however, the part-cylindrical portion of the needle is formed by moving the wire parallel to the longitudinal axis of the needle (i.e. at an angle θ–x=0), as this arrangement minimises the component of the reaction forces acting perpendicular to the injection path during insertion of the needle into the skin.

These preferred embodiments of the injection apparatus allow injection to a fixed depth to be achieved accurately. The system has several advantages over prior art methods of injection. First, as the needle extends under the skin surface the site of entry of the needle is not near the site of injection. This may be important in optical interrogation of assays. Secondly, the channel depth of the needle in the skin is much larger than the injection depth. This means that a seal is formed between the skin and the needle, so that the material to be injected does not travel along the outside of the needle to the outside of the skin. Thirdly, injected material is often spread out because of the pressure of injection and the possibility of migration through tissue. This is particularly significant in vertical injection into the skin, where material often reaches the fat tissue below the skin which has a low resistance to flow. Using the present injection apparatus, even if the injected material is spread out, it will be spread horizontally at the same depth. When the apparatus is used to inject assay sensors, this has the advantage that there is no stray signal from sensors at depths other than the required depth.

Further, the use of the needles described herein in conjunction with the described injection apparatuses allows the depth of injection to be reliably reproduced, particularly when injecting substances or particles requiring a large lumen diameter needle to be used. A particular application for which this advantage is important is the implantation of sensor particles in the skin in order to carry out measurement of blood glucose concentration based on fluorescence lifetime spectroscopy, as the sensor must be placed immediately below the basement membrane which separates the dermis from the epidermis in order that the sensor may measure the glucose concentration in a vasculised region of the skin and that the sensor may be optically interrogated.

In an alternative embodiment, the tiltable base plate 24 may be replaced by an inclined surface which is pressed against the skin surface to provide a fixed-depth injection path parallel to the inclined surface. The inclined surface may be the surface of a cone, the apex of the cone being pressed against the skin surface, or may be the surface of a flat plate pressed at an angle against the skin.

Figure 7:
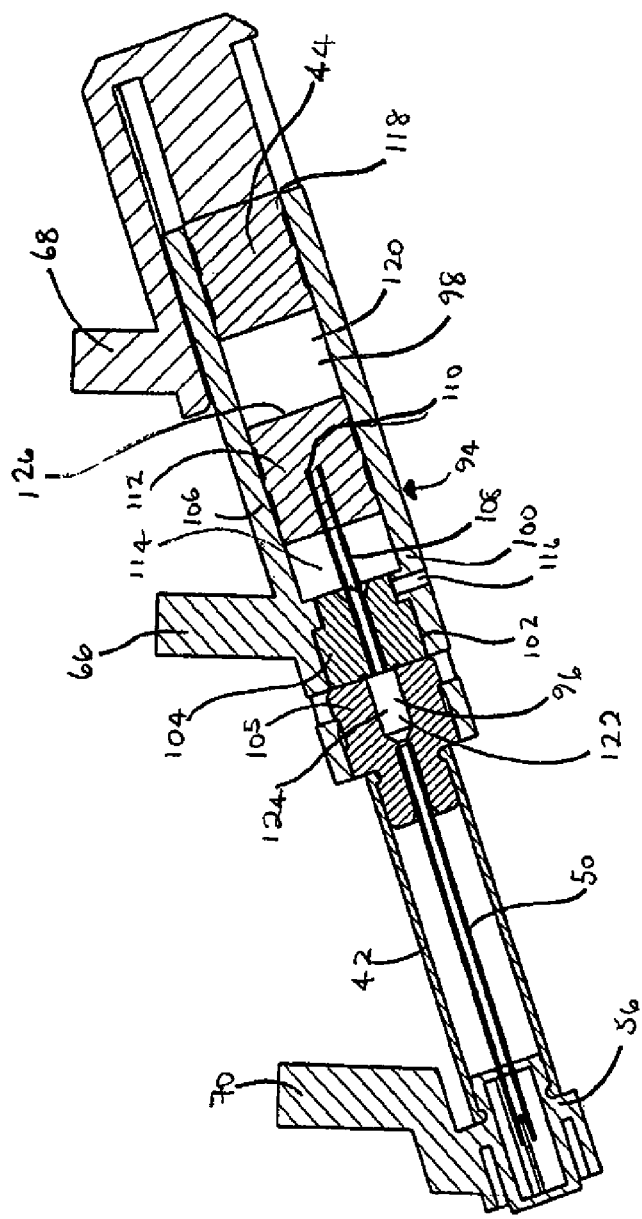
FIG. 7 is an enlarged view of the syringe component of the apparatus as shown in FIG. 4.
Figure 8:
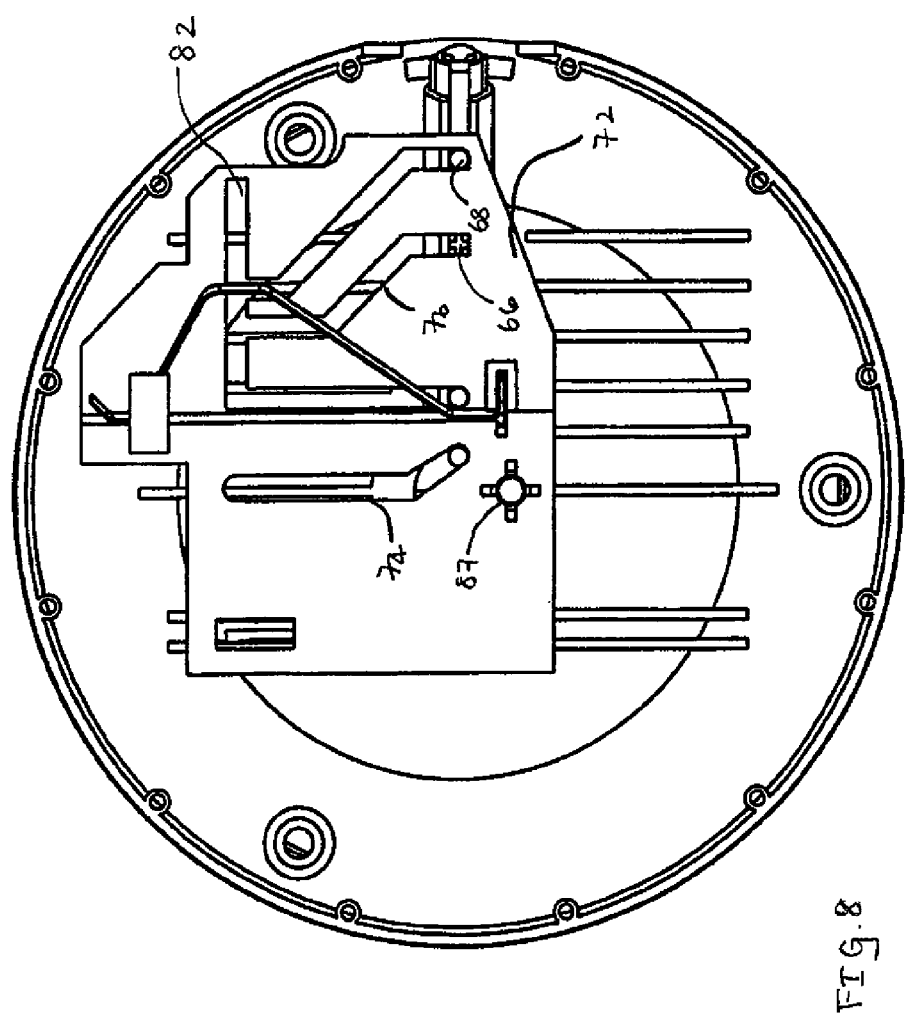
FIG. 8 is a plan view of the apparatus as shown in FIG. 6.

FIGS. 4 and 7 show a double chamber syringe 94 suitable for use with a preferred embodiment of the invention. This syringe 94 is used for injecting powder suspended in a liquid 98 which is kept separate from the powder 96 until the moment of injection. In alternative embodiments, the syringe may contain a liquid and two powders, two liquids and a powder, a solid dose and a liquid, a solid dose and a plunger, or other materials to be injected. Such a syringe is described in detail in WO003/072172.

Whilst the invention has been described with reference to the illustrated embodiments, it is to be appreciated that many modifications and variations are possible within the scope of the invention.

The invention claimed is:

1. An injection apparatus for making an injection at a predetermined depth in skin, comprising:
a skin positioning member for positioning a patch of skin within an area of skin to hold the patch of skin in a defined position;
an injection needle comprising a tip, at least one bevel and a heel together forming a point at a distal end thereof, and a shaft portion immediately proximal of said heel having a longitudinal axis, including a lumen extending along the longitudinal axis, wherein the at least one bevel is formed between said tip and said heel such that a lumen opening is defined from the tip to a proximal end of the lumen opening located distal of the heel;
and an injection needle movement guide proximate the injection needle to guide said injection needle for movement from a parking position above said skin positioning member to an injection position in which the distal end of the needle lies at a predetermined distance below said skin positioning member;
wherein:
a length of the lumen opening of the needle from the tip of the needle to the proximal end of the lumen opening is in a range from 5 to 15 times an outer diameter of the shaft of the needle and the length of the lumen opening of the needle is measured parallel to the longitudinal axis of the needle;
wherein at least a part of the point of the injection needle is formed substantially parallel to the longitudinal axis of the needle.

2. The injection apparatus according to claim 1, further comprising a housing containing: the injection needle mounted for guided movement from a parked position to an operative position; a detachable marker unit mounted to said housing and so positioned that said needle passes therethrough to reach said operative position; and a securing member coupled to the marker unit to secure said marker unit at an injection site prior to the making of an injection, whereby said apparatus can in use be positioned at an injection site, said needle can be moved to said operative position to make an injection and said housing can be removed leaving said marker unit at the injection site to mark the position thereof.

3. The injection apparatus according to claim 2, wherein said marker unit comprises a plate having an aperture therein through which the needle passes in use.

4. The injection apparatus according to claim 3, wherein said aperture has a maximum dimension of 2 mm or less.

5. The injection apparatus according to claim 1, wherein the tip of the injection needle is closer to the longitudinal axis of the shaft portion than is the outside of the shaft portion.

6. The injection apparatus according to claim 1, in which the outer diameter of the shaft of the injection needle is between 0.5 mm to 1.5 mm.

7. The injection apparatus according to claim 1, in which the outer diameter of the shaft of the injection needle is 1.1 mm.

8. The injection apparatus according to claim 1, in which the length of the lumen opening of the injection needle is between 5.5 mm and 16.5 mm.

9. The injection apparatus according to claim 1, in which at least a part of the point of the injection needle is in the form of a part-cylinder.

10. The injection apparatus according to claim 9, in which the distance perpendicular to the longitudinal axis of the injection needle from the tip to the bevel face at the part-cylinder is at least 50% of the outer diameter of the shaft of the needle.

11. The injection apparatus according to claim 1, wherein the distal end of the needle lies within the skin.

12. The injection apparatus according to claim 1, wherein the length of the lumen opening of the needle is in a range from 8 to 12 times an outer diameter of the shaft of the needle.

13. The injection apparatus according to claim 9, further comprising a second bevel, wherein the bevel and the second bevel are on opposite longitudinal ends of the part-cylinder and the bevel and the second bevel are formed at similar angles with respect to the longitudinal axis.

14. An injection apparatus for making an injection at a predetermined depth in skin comprising: a skin positioning member for positioning on a patch of skin within an area of skin to hold the patch of skin in a defined position, an injection needle comprising a point having a tip at a distal end thereof and a shaft portion immediately proximal to said point, the shaft portion having a longitudinal axis, and an injection needle movement guide proximate the injection needle to guide said injection needle for movement from a parking position above the skin beside said skin positioning member to slide beneath said skin positioning member to an injection position in which the distal end of the needle lies at a predetermined distance below said skin positioning member; wherein: the tip of the injection needle is closer to the longitudinal axis of the shaft portion than is an outside of the shaft portion;

wherein the tip of the injection needle is closer to the longitudinal axis of the shaft portion than is the outside of the shaft by bending the tip of the injection needle.

* * * * *